United States Patent [19]

Kurth

[11] Patent Number: 5,503,990

[45] Date of Patent: Apr. 2, 1996

[54] PREPARATION OF HEALTH FOOD SUPPLEMENT PRODUCT

[76] Inventor: Gerhard D. Kurth, 1117 Putnam Ave., Riverside, Conn. 06878

[21] Appl. No.: 302,518

[22] Filed: Nov. 9, 1994

[51] Int. Cl.⁶ ................................................ C12P 21/06
[52] U.S. Cl. ........................................ 435/68.1; 424/528
[58] Field of Search ............................ 435/68.1; 424/528

[56]  References Cited

U.S. PATENT DOCUMENTS

| | | | |
|---|---|---|---|
| 3,625,896 | 12/1971 | Kirk et al. | 428/403 |
| 4,350,682 | 9/1982 | Balassa | 424/64 |
| 4,656,137 | 4/1987 | Balassa | 435/267 |
| 4,776,861 | 10/1988 | Frushour | 51/293 |
| 4,822,607 | 4/1989 | Balassa et al. | 424/548 |
| 4,828,582 | 5/1989 | Fushour | 51/293 |
| 4,871,551 | 10/1989 | Spencer | 426/2 |
| 5,284,155 | 2/1994 | Treadwell et al. | 623/16 |

*Primary Examiner*—Herbert J. Lilling

[57]  ABSTRACT

The present invention relates to a significant improvement in the preparation of a pharmaceutically purified and proven effective product of powdered hormone-free bovine cartilage for the treatment of a number of different cancers, such as those disclosed in U.S. Pat. No. 4,822,607. This improvement in the process of preparation accomplishes this by producing a more effective product because the novel process produces particles of a more uniform size. The novel process is more efficient because it is less costly and less time consuming to prepare than the presently used process.

6 Claims, No Drawings

PREPARATION OF HEALTH FOOD SUPPLEMENT PRODUCT

FIELD OF THE INVENTION

The present invention relates to an improvement in the preparation of a pharmaceutical grade of hormone-free bovine cartilage described and patented by Balassa & Prudden in his U.S. Pat. No. 4, 822,607, issued 18 Apr. 1989 and also described in the publication The Journal of Biological Response Modifiers, Vol. No. 6, 1985 by the same J. F. Prudden, the improvement of the present invention allows for a much more uniform final product anda process for producing the product more efficiently and more cost effective.

CROSS-REFERENCES TO RELATED ART

The following art has been found to be related to the field of the present invention but in no way does any of the herein cited references anticipate or even suggest the novel advance in the method, that is made by the process of the present invention.

U.S. Pat. No. 4,822,607 and the article by J. F. Prudden in the Journal of Biological Response Modifiers, Vol. 6, 1985, the process described therein will be compared to the novel process of the present invention later in this application "The Treatment of Human Cancer with Agents Prepared from Bovine Cartilage", Written by John F. Prudden, Department of Surgery, Doctors Hospital, New York, N.Y., Jun. 21, 1985 printed by Journal of Response Modifiers and published by Raven Press, will also be compared to the novel process of the present invention.

OBJECTS OF THE INVENTION

The object of the present invention is to provide a novel process to prepare a pharmaceutical grade hormone-free bovine cartilage product. Another object of the present invention is to provide a novel process of preparing a pharmaceutical grade bovine cartilage product that eliminates the use of ball milling to achieve desired particle size Various other objects, advantages and features of the present invention will become apparent to those skilled in the art from the previous and following discussion, taken in conjunction with the examples, which constitute a part hereof.

SUMMARY OF THE INVENTION

The present invention is a significant improvement in the preparation of extremely finely divided bovine cartilage to form a novel hormone-free particle pharmaceutical grade product of uniform size for the treatment of existing cancers as disclosed in the above referenced U.S. Pat. No. 4,822,607

The improvement in the presently used processes to prepare bovine cartilage in dosage form that is disclosed in J. F. Prudden's works, supra., is by the elimination of the use of the milling as presently used. In the presently available bovine cartilage preparation processes, the final step is carried-out by common ball milling, which produces a non-uniform size that is unacceptable to the present invention. The finely divided purified pharmaceutical grade bovine cartilage that is necessary to attain the effectiveness of the product prepared by the process of the present invention is accomplished by a cryogenic process which delivers a product that is much more uniform in size.

The product produced by the process of the present invention is novel because of its predictabilityin particle size and because the process reduces time and effort in producing the product.

DESCRIPTION OF THE PREFERRED EMBODIMENT OF THE PRESENT INVENTION

The raw cartilage may be prepared, using cartilage in sizes up to about 750 microns and by any of the suitable methods as taught, that produce a particle size of between about 10 and about 150 microns. These methods are described in U.S. Pat. No. 3,400,199 (U.S. Pat. No. Re. 28,093), U.S. Pat. No. 3,966,908 and U.S. Pat. No. 4,822,607

The new improved process of the present invention is accomplished by producing considerably more reliable and predictably uniform size particles of the bovine hormone-free cartilage product, by replacing the final step of each of the processes referred supra., namely the ball milling with the aerospace technology of impact milling coupled with cryogenic treatment. This treatment is carded-out .with the use of the Vortec Products Company, Long Beach, Calif., Model M-1, "Vortec Impact Mill" These steps will be discussed in detail later in this specification. In the art and in the present invention, the average size of each finely divided hormone-free bovine cartilage particle that is to be used in Step 1, is not critical and successful extracts have been prepared using particle sizes of from about 8 mm sq. to about 12 mm sq. However, it has been found that more effective extraction can be obtained with the use of bovine cartilage size of between about 1 mm and 3 mm sq.

DETAILED DESCRIPTION OF THE PROCESS OF THE PRESENT INVENTION

In order to more deafly point out the improvement of the present invention, a comparison is made in the following Tables, between the process of the art, as being used at this time and the process of the present invention, which accomplishes all of the objects of the invention as pointed out supra.

TABLE 1

|        | Process of the Art                              | Process of the Present Inention                |
|--------|-------------------------------------------------|------------------------------------------------|
| Step 1 | Chopped Bovine Trachea in a size of 8 mm to 12 mm | Chopped Bovine Trachea in a size of about 1 mm to 3 mm |
| Step 2 | Enzymatic Digestion                             | Enzymatic Digestion                            |
| Step 3 | Lipid (fat) Removal                             | Lipid (fat) Removal                            |
| Step 4 | Ball Milling at ambient temperature             | Jet Impact Milling at about −50 C.             |

As can be seen from Table 1 supra., Step 1 differs somewhat and, Steps 2 and 3 differ very little, However, Step 4 is in which the present invention lies. An explanation of Steps 1, 2, 3 and 4 follows:

Step 1. Raw hormone-free bovine trachea cartilage is washed and frozen at −70° C. to prevent bacterial load. The trachea is thawed and mechanically trimmed of all adhering tissues, cut into small chunks of a size of between 8 mm to 12 mm for the process of the art and to between about 1 mm and about 3 mm in the process of the present invention for more efficient processing.

Step 2. The Enzymatic Digestion is accomplished by subjecting the chopped trachea to the enzymatic action of Pepsin in order to digest the unwanted protein. Since Pepsin is acid in its pH, the pH in this step must be constantly monitored and adjusted in order to maintain a constant pH of between 6.5 and 8.0. When the enzymatic digestion is complete, the treated chopped trachea is carried to Step 3, where the lipid (fat) is removed.

Step 3. the enzyme treated chopped trachea is subjected to the fat is removed by the use of the solvent Acetone. As can be seen, up to this point the presently used method and the method of the present invention are relatively similar except for the beginning trachea size, as discussed, supra. The present invention lies in Step 4 below.

Step 4 is the step that produces the final product that is to be packaged and delivered to the public for ingestion. In the present art the cleaned chopped trachea is subjected to ball milling, which is well known to the those skilled in the art. Ball milling produces a reduction of size but the uniformity of particle size is not desirable and reliable and requires additional classification to remove remaining large particles. This results in a process that is much more time consoming than the process of the present invention, in addition, the process that is presently used is more expensive than the process of the present invention The process of the present invention has discovered that the final product size and uniformity is dramatically improved by subjecting the cleaned chopped trachea to Impact Jet Milling in Step 4. Impact Jet Milling is a new process developed by the Vortec Product Company of Long Beach, Calif., with the use of its model M-1 Vortec Milling Machine. This step involves the air swept machine relying on particle kinetic energy for particle size reduction. It accelerates each particle mechanically and thus directs particles to impact on stationary impact blocks. The high energy, single impact fractures particles along their natural grain line. After impact, the particles are transported via air flow to a collection cyclone. Control over particle size reduction is attained by varying the speed of the machine to provide a suitable particle kinetic energy level that effect each particle. Size reduction is enhanced by increasing particle kinetic energy level. Conversely it is minimized by reducing kinetic energy.

The impact mill maximizes product yield by controlling the quantity of undersize particulars produced as follows, kinetic energy is impacted to each particle in proportion to the particle size. Since the propensity for fracture varies with the partial kinetic energy, small particles in feed stock will fracture less than larger particles. The powdered trachea is removed from the Impact Jet Mill after a single impact. Thus, particles that have been reduced to the desired size may be removed immediately after being produced. Energy is not wasted because it is supplied only to particles requiring size reduction. The resulting final product is produced more efficiently. Because the cost of production is reduced and because of the uniformity and smaller size of the resulting product, it is more effective.

While the above description contains many specificities, the reader should not construe these as limitations on the scope of the invention, but merely as exemplification of a preferred embodiment. Those skilled in the art will envision that many other possible variations are within the scope of the present invention. For example, skilled artisans will readily be able to change the dimensions and materials of the various embodiments. They can make variations on the design of the present invention. Accordingly, the reader is requested to determine the scope of the present invention by the scope of the appended claims and the legal equivalents, and not by the examples given.

What is claimed is:

1. A process of preparing a finely divided bovine trachea cartilage of uniform size comprising the steps of:
   a. providing said cartilage in a chopped form,
   b. subjecting said chopped cartilage to an enzymatic reduction process to remove protein and any fat that may be remaining,
   c. removing any fat that may be remaining from enzyme reduced cartilage,
   d. reducing the size of the cartilage, from which, any fat has been removed by subjecting said cartilage in an impact jet milling process at a cryogenic temperature of about −50° C. to attain uniform particle sizing.

2. The process of claim 1 wherein said trachea cartilage is chopped to a size of from about 1 mm to about 3 mm sq prior to enzymatic digestion.

3. The process of claim 1, wherein protein from said cartilage is removed by subjecting said cartilage to enzymatic digestion with pepsin.

4. The process of claim 1, wherein fat is removed from said protein reduced cartilage by subjecting said pepsin reduced cartilage to the action of acetone.

5. The process of claim 1, wherein said fat removed cartilage is milled at a cryogenic temperature of about −50° C. to a uniform particle size said cartilage to size reduction in a impact jet mill.

6. The process of claim 1, wherein said bovine trachea cartilage is chopped to a size from about 1 mm to about 3 mm sq.; said chopped cartilage is treated with a solution of acetic acid and pepsin at about 50° to 55° C. for about 5 hours, the pH is maintained at the referenced temperature by adjustment with about 1 mole of HCl and NaOH, said treated cartilage is washed thoroughly by covering said cartilage with deionized cold water at about 5° to 15° C.; said cold wash washed cartilage is suspended in acetone and stirred for about 1 hour at standard laboratory conditions, the supernatant liqueur is removed and the step is repeated two more times; the acetone treated cartilage is dried in a vacuum at about 50° to 60° C. and the dried cartilage is impact jet milled at a cryogenic temperature of about −50° C. to the desired uniform size.

* * * * *

UNITED STATES PATENT AND TRADEMARK OFFICE
CERTIFICATE OF CORRECTION

PATENT NO. : 5,503,990
DATED : April 2, 1996
INVENTOR(S) : Kurth

It is certified that error appears in the above-indentified patent and that said Letters Patent is hereby corrected as shown below:

The title page should be deleted and substitute therefor the attached title page.

Signed and Sealed this

Twentieth Day of August, 1996

Attest:

BRUCE LEHMAN

*Attesting Officer*   *Commissioner of Patents and Trademarks*

United States Patent [19]

Kurth

[11] Patent Number: 5,503,990

[45] Date of Patent: Apr. 2, 1996

[54] PREPARATION OF HEALTH FOOD SUPPLEMENT PRODUCT

[76] Inventor: Gerhard P. Kurth, 1117 Putnam Ave., Riverside, Conn. 06878

[21] Appl. No.: 302,518

[22] Filed: Nov. 9, 1994

[51] Int. Cl.$^6$ ................................................ C12P 21/06
[52] U.S. Cl. ................................ 435/68.1; 424/528
[58] Field of Search ........................ 435/68.1; 424/528

[56] References Cited

U.S. PATENT DOCUMENTS

| | | | |
|---|---|---|---|
| 3,625,896 | 12/1971 | Kirk et al. | 428/403 |
| 4,350,682 | 9/1982 | Balassa | 424/64 |
| 4,656,137 | 4/1987 | Balassa | 435/267 |
| 4,776,861 | 10/1988 | Frushour | 51/293 |
| 4,822,607 | 4/1989 | Balassa et al. | 424/548 |
| 4,828,582 | 5/1989 | Fushour | 51/293 |
| 4,871,551 | 10/1989 | Spencer | 426/2 |
| 5,284,155 | 2/1994 | Treadwell et al. | 623/16 |

*Primary Examiner*- Hebert J. Lilling
*Attorney, Agent, or Firm*- James J. McKeever, Esq.

[57] ABSTRACT

The present invention relates to a significant improvement in the preparation of a pharmaceutically purified and proven effective product of powdered hormone-free bovine cartilage for the treatment of a number of different cancers, such as those disclosed in U.S. Pat. No. 4,822,607. This improvement in the process of preparation accomplishes this by producing a more effective product because the novel process produces particles of a more uniform size. The novel process is more efficient because it is less costly and less time consuming to prepare than the presently used process.

6 Claims, No Drawings